(12) United States Patent
Bastian et al.

(10) Patent No.: US 7,960,110 B2
(45) Date of Patent: Jun. 14, 2011

(54) DETECTION OF CHROMOSOMAL REGION COPY NUMBER CHANGES TO DIAGNOSE MELANOMA

(75) Inventors: Boris Bastian, Mill Valley, CA (US); Daniel Pinkel, Lafayette, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/941,002

(22) Filed: Nov. 15, 2007

(65) Prior Publication Data
US 2008/0182257 A1 Jul. 31, 2008

Related U.S. Application Data

(60) Provisional application No. 60/859,408, filed on Nov. 15, 2006.

(51) Int. Cl.
*C12Q 1/68* (2006.01)
(52) U.S. Cl. .......................................................... 435/6
(58) Field of Classification Search .................... None
See application file for complete search history.

(56) References Cited

U.S. PATENT DOCUMENTS

| | | | |
|---|---|---|---|
| 6,261,775 | B1 | 7/2001 | Bastian et al. |
| 6,455,258 | B2 | 9/2002 | Bastian et al. |
| 6,465,180 | B1 | 10/2002 | Bastian et al. |
| 6,783,944 | B2 | 8/2004 | Bastian |
| 2001/0038833 | A1 | 11/2001 | Rybak et al. |
| 2003/0073119 | A1 | 4/2003 | Bastian et al. |
| 2005/0026190 | A1 | 2/2005 | Sokolova et al. |
| 2006/0211019 | A1 | 9/2006 | Halling et al. |
| 2007/0059747 | A1 | 3/2007 | Bastian et al. |

FOREIGN PATENT DOCUMENTS

| | | |
|---|---|---|
| EP | 1 035 215 A2 | 9/2000 |
| WO | WO 00/61814 A | 10/2000 |
| WO | WO 02/066685 A | 8/2002 |
| WO | WO 2007/028031 A2 | 3/2007 |

OTHER PUBLICATIONS

Mao et al (British Journal of Dermatology, 2001, 145: 117-122).*
Wang et al (Cancer Research, May 2001, 4169-4174).*
Kawanishi et al (J Hum Genet, 2000, 45(1): 24-30).*
Bastian, Boris C. et al.; "Gene Amplifications Characterize Acral Melanoma and Permit the Detection of Occult Tumor Cells in the Surrounding Skin"; 2000, *Cancer Research*, vol. 60, pp. 1968-1973.
Bastian, Boris C. et al.; "Classifying Melanocytic Tumors Based on DNA Copy Number Changes"; 2003, *American Journal of Pathology*, vol. 163, No. 5, pp. 1765-1770.
Curtin, John A. et al.; "Distinct Sets of Genetic Alterations in Melanoma"; 2005, *New England Journal of Medicine*, vol. 353, No. 20, pp. 2135-2147.

Maldonado Janet L. et al.; "Determinants of BRAF Mutations in Primary Melanomas"; 2003, *Journal of the National Cancer Institute*, vol. 95, No. 24, pp. 1878-1880.
Van Dijk, Marcory et al.; "Distinct Chromosomal Aberrations in Sinonasal Mucosal Melanoma as Detected by Comparative Genomic Hybridization"; 2003, *Genes, Chromosomes & Cancer*, vol. 36, pp. 151-158.
Veenhuizen, Karin C. W. et al.; "Quality Assessment by Expert Opinion in Melanoma Pathology: Experience of the Pathology Panel of the Dutch Melanoma Working Party"; 1997, *Journal of Pathology*, vol. 182, pp. 266-272.
Kim, Minjung, "Comparative oncogenomics identifies NEDD9 as a melanoma metastasis gene," *Cell* (Jun. 30, 2006) 125: 1269-1281.
Tschentscher, Frank, "Identification of chromosomes 3, 6, and 8 aberrations in uveal melanoma by microsatellite analysis in comparison to comparative genomic hybridization," *Cancer Genetics and Cytogenetics* (2000) 122: 13-17.
Balazs, M., et al,. "Chromosomal Imbalances in Primary and Metastatic Melanomas Revealed by Comparative Genomic Hybridization," *Cytometry*, vol. 46, pp. 222-232 (2001).
Bastian, B., et al., "Genomic Approaches to Skin Cancer Diagnosis," *Arch Dermatol*, vol. 137, pp. 1507-1511 (Nov. 2001).
Blixt, A., et al., "The Two-Exon Gene of the Human Forkhead Transcription Factor FREAC-2 (FKHL6) Is Located at 6p25.3," *Genomics*, vol. 53(3), pp. 387-390 (Nov. 1, 1998).
Casorzo, L., et al., "Fluorescence in situ hybridization (FISH) evaluation of chromosomes 6, 7, 9 and 10 throughout human melanocytic tumorigenesis," *Melanoma Research*, vol. 15(3), pp. 155-160 (Jun. 2005).
Healy, E., et al., "Alleotypes of Primary Cutaneous Melanoma and Benign Melanocytic Nevi," *Cancer Research*, vol. 56, pp. 589-593 (Feb. 1, 1996).
Lindqvist, A-K., et al., "A Susceptibility Locus for Human Systemic Lupus Erythematosus (hSLE1) on Chromosome 2q," *Journal of Autoimmunity*, vol. 14(2), pp. 169-178 (Mar. 2000).
Matsuta, M., et al., "Detection of numerical chromosomal aberrations in malignant melanomas using fluorescence in situ hybridization," *Journal of Cutaneous Pathology*, vol. 24(4), pp. 201-205 (Apr. 1997).
Namiki, T., et al., "Genomic alterations in primary cutaneous melanomas detected by metaphase comparative genomic hybridization with laser capture or manual microdissection: 6p gains may predict poor outcome," *Cancer Genetics and Cytogenetics*, vol. 157(1), pp. 1-11 (Feb. 2005).
Patel, K., et al., "Prediction of prognosis in patients with uveal melanoma using fluorescence in situ hybridization," *Br J Ophthalmol*, vol. 85(12), pp. 1440-1444 (2001).
European Supplemental Search Report dated Jul. 16, 2009, issued in EP 06802823.2.
European Office Action dated Nov. 2, 2009, issued in EP 06802823.2.
International Search Report dated Jun. 11, 2007 from related International Application No. PCT/US06/34251 [ABOTP009WO].

* cited by examiner

*Primary Examiner* — Sean E Aeder
(74) *Attorney, Agent, or Firm* — Kilpatrick Townsend & Stockton LLP

(57) ABSTRACT

This invention provides methods of detecting melanoma. The methods comprises detecting a gain or loss of certain chromosomal regions that undergo copy number changes in melanoma.

8 Claims, 2 Drawing Sheets

US 7,960,110 B2

DETECTION OF CHROMOSOMAL REGION COPY NUMBER CHANGES TO DIAGNOSE MELANOMA

CROSS-REFERENCE TO RELATED APPLICATIONS

This application claims benefit of U.S. provisional application No. 60/859,408; filed: Nov. 15, 2006, which is herein incorporated by reference.

STATEMENT AS TO RIGHTS TO INVENTIONS MADE UNDER FEDERALLY SPONSORED RESEARCH OR DEVELOPMENT

This invention was made with Government support under grant nos. CA95300 and CA094963 awarded by the National Institutes of Health. The Government has certain rights in this invention.

BACKGROUND OF THE INVENTION

The incidence and mortality of melanoma has been increasing more rapidly than any other malignancy except lung cancer in women. Although many cases can be classified reliably with current pathological criteria, there is a significant subset of cases in which no consensus can be reached even among expert pathologists. The effect of the ambiguity on standard clinical practice is illustrated in a study from The Netherlands. An expert panel reviewed 1069 consecutive melanocytic lesions that had been submitted for review by clinical pathologists in order to identify the most common diagnostic problems. In 14% (22/158) of the cases that had been initially classified as invasive melanoma the panel considered the lesions as benign, and in 16.6% (85/513) the panel considered malignant what had been diagnosed as benign (Veenhuizen et al., *J Pathol.* 182:266-72. 1997).

Diagnostic ambiguity has significant adverse consequences for patients. Misclassifying a melanoma as benign may be fatal, and diagnosing a benign lesion as malignant may result in significant morbidity. Current medical practice with equivocal cases usually is to consider them as malignant. However, the morbidity of the therapeutic options—wide re-excision, sentinel lymph node biopsy, and adjuvant alpha-interferon—coupled with the diagnostic uncertainty frequently leads to pursuing a less aggressive treatment regimen. Typically this includes a limited re-excision and close clinical follow-up. Thus patients with benign lesions suffer the side effects of a still significant surgery and the emotional strain of the diagnosis, while those patients that in fact have a melanoma may not receive the optimal treatment. Currently there is no method to definitively resolve these ambiguities. A diagnostic test that could reduce these uncertainties would have a significant positive clinical impact.

Previous studies have shown that melanomas differ from nevi by the presence of frequent gains or losses of particular chromosomal regions. Comparative genomic hybridization (CGH) of primary melanomas has identified losses at 6q, 8p, 9p, and 10q and gains at 1q, 6p, chromosome 7, 8q, 17q, and 20q to be the most common DNA copy number changes in melanoma (Bastian et al, *Am J Pathol.* 163:1765-70, 2003). However, there is a need for further refinement of diagnostic techniques that evaluate chromosome copy number changes so that a melanoma can be more accurately characterized. This invention addresses that need.

BRIEF SUMMARY OF THE INVENTION

The present invention is based on the discovery that certain chromosomal regions (also referred to herein as "subregions") undergo copy number changes in melanoma. Thus, in some aspects, the invention provides a method of detecting a melanoma in a patient, the method comprising: contacting a nucleic acid present in a biological sample from the patient with a probe that selectively hybridizes to a chromosomal region selected from the group consisting of 1q21, 1q32, 1q42, 5p15, 6p24, 6p23, 6p22, 6p21, 7q36, 9p24, 10q21, 10q23.3-10q24.1 (e.g., from about 89,698,198 to about 93,052,778), 10q25, 12q15, and 21q21; and detecting a gain or loss in the copy number of the chromosomal region, thereby detecting the melanoma. In some embodiments, the change in copy number is a gain of 1q21, 1q32, 1q42, 5p15, 6p21, 6p22, 6p23, 6p24, 7q36, or 12q15. In other embodiments, the change is a loss of 9p24, 10q21, 10q23.3-10q24.1 (e.g., from about 89,698,198 to about 93,052,778), 10q25, or 21q21.

The analysis is performed by evaluating nucleic acids from a biological sample from the patient. The biological sample is obtained from a tissue is suspected of containing, or contains, melanoma cells. In some embodiments, the biological sample is a skin sample. In other embodiments, the biological sample may be from a metastatic site, e.g., from lymph node, lung, liver, adrenal gland, or bone. In other embodiments, the biological sample may be blood.

Change in copy number can be assessed using a variety of methods known in the art. Thus, in some embodiments, the contacting step comprises an in situ hybridization. In other embodiments, the change in copy number is determined using comparative genomic hybridization. In still other embodiments, the change in copy number is determined using a quantitative amplification reaction, e.g., a quantitative polymerase chain reaction (PCR).

A probe for use in the invention can be any probe that selectively hybridizes to the region of interest. In some embodiments, the probe selectively hybridizes to a gene listed in Table 1.

DETAILED DESCRIPTION OF THE INVENTION

Figure 1:
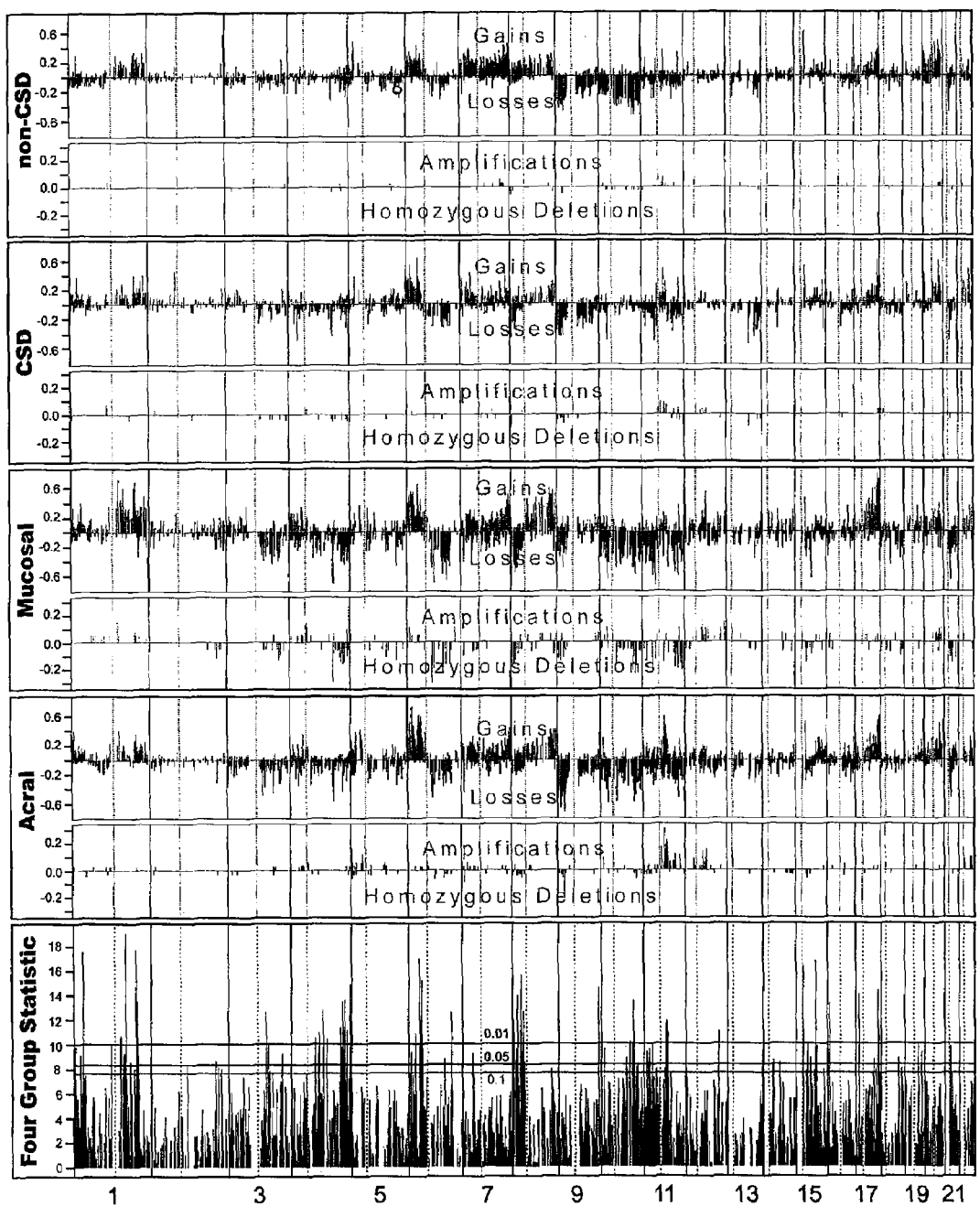
FIG. 1 shows frequency plots of the DNA copy number changes in melanoma groups. Two histograms are shown for each group of melanoma. The upper plot show low-level gains and losses and the lower panel shows amplifications and homozygous deletions for each type. Vertical dashed lines represent the centromere location. The X axis represents genomic position with the BACs ordered by position in the genome beginning at 1p and ending at 22. The Y axis represents the fraction of the samples with a given clone altered. The bottom plot displays the statistical differences between the copy number changes in the four groups. The magnitude of F-statistic is shown as the height of the vertical bars and their global significance is indicated with horizontal dashed lines indicating maxT adjusted p-value cutoff (0.01, 0.05, 0.1).
Figure 2:
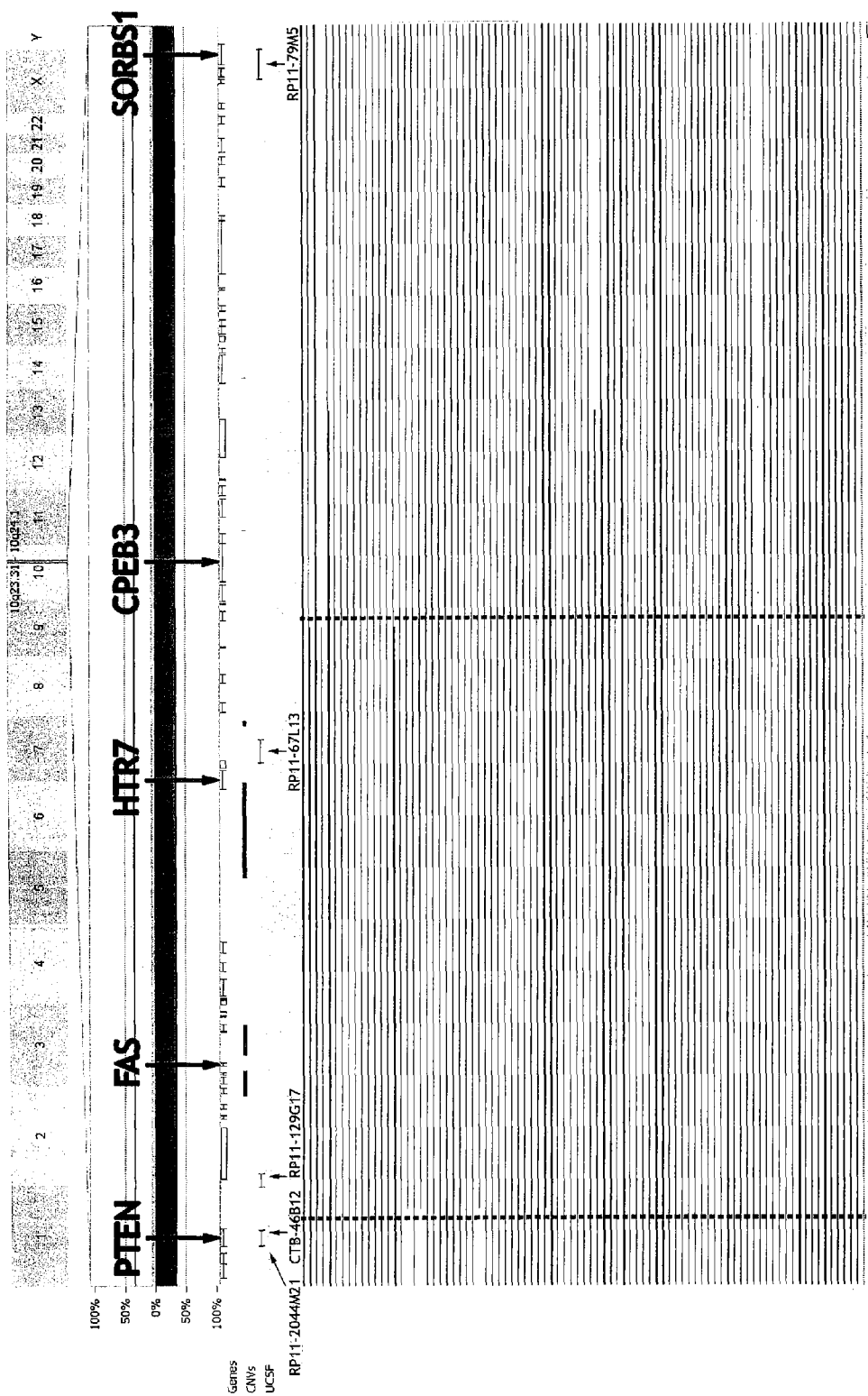
FIG. 2 depicts a minimally deleted region on chromosome 10q: Shown are copy number decreases as assessed by array CGH at an interval of chromosome 10 at bands 10q23.31 to 10q24.1. The thick horizontal bar toward the top of the diagram represents a histogram, indicating that this interval is lost in approximately 37% of melanomas (thick line) and gained in less than 5% (thin gray line). On the line underneath, the genes within the regions are shown and some are labeled to serve as landmarks. The line segments underneath represent genomic regions of known copy number variations (CNVs). Underneath that, the position of the BACs represented on the CGH array is shown. The horizontal lines in the bottom half of the chart display the copy number alterations in individual melanoma samples with thin lines indicating heterozygous losses (log 2ratios between −0.3 and −0.5) and thick lines indicate homozygous deletions (log 2ratios<−0.5). The minimally deleted region in this area is indicated by dashed vertical lines and is restricted to the two BACs RP11-129G17 and RP11-67L13. The two BACs that contain PTEN sequences (RP11-2044M21 & CTB-46B12) are not included in this deletion.

The invention is based on the identification of particular regions of chromosomes that undergo copy number changes in melanoma. To facilitate understanding the invention, a number of terms are defined below.

Definitions

The terms "melanoma" or "cutaneous melanoma" or "malignant melanoma" refer to malignant neoplasms of melanocytes, which are pigment cells present normally in the epidermis, in adnexal structures including hair follicles, and sometimes in the dermis, as well as extracutaneous sites such as the mucosa, meninx, conjuctiva, and uvea. There are at least four types of cutaneous melanoma: lentigo maligna melanoma, superficial spreading melanoma (SSM), nodular melanoma, and acral lentiginous melanoma (AM). Cutaneous melanoma typically starts as a proliferation of single melanocytes, e.g., at the junction of the epidermis and the dermis. The cells first grow in a horizontal manner and settle an area of the skin that can vary from a few millimeters to several centimeters. As noted above, in most instances the transformed melanocytes produce increased amounts of pigment so that the area involved can easily be seen by the clinician.

In the context of this application "acral melanoma" refers to melanoma occurring on the non-hair-bearing skin of the palms or soles or under the nails. A subset of acral melanomas are "acral-lentiginous melanomas"

The term "mucosal melanoma" refers to tumors arising on mucosal membranes.

"CSD melanoma" as used herein refers to melanoma arising from skin with chronic sun-induced damage; and "NCSD melanoma" as used herein refers to melanoma arising from skin without chronic sun-induced damage. The distinction between the "CSD" and "NCSD" groups in the instant application is based on the presence or absence on microscopy of marked solar elastosis of the dermis surrounding the melanomas. In all but a few cases, melanomas associated with chronic sun-induced damage (CSD) occur on the face and distal extremities such as the forearms, dorsal hands, shins and calfs. These melanomas typically occur in individuals older than 50 years of age, and microscopically, have an intraepidermal component in which melanocytes are arranged as solitary units rather than nests. In addition, these melanomas tend to have an atrophic epidermis with the effacement of the rete ridges. A subset of the CSD melanomas is lentigo maligna melanomas. By contrast melanomas that were not associated with chronic sun-induced damage (NCSD) occur on the trunk and proximal extremities such as thighs and upper arms. The NCSD melanomas typically show an intraepidermal component in which melanocytes are arranged as nests rather than solitary units and display considerable upward scatter (pagetoid spread). Many of the NCSD melanomas are superficial spreading melanomas.

Chronic sun-induced damage is defined as having a CSD score greater than CSD 2. The scores are obtained by determining the degree of solar elastosis on hematoxylin-and-eosin (H&E) stained sections of normal skin surrounding the melanomas at 100-200× magnification using the following system (Landi et al., *Science* 313:521-522, 2006).

CSD 0: absence of elastotic fibers; CSD 0+: rare elastotic fibers discernible only at 200× magnification;

CSD 1: scattered elastotic fibers lying as individual units, not as bushels, between collagen bundles;

CSD 2: densely scattered elastotic fibers distributed predominantly as bushels rather than individual units;

CSD 3: amorphous deposits of blue-gray material with lost fiber texture; "−" only focal formation of amorphous deposits; "+" very large agglomerates of diffuse basophilic material.

The term "melanocytic lesion" refers to an accumulation of melanocytes that can undergo a benign, locally aggressive, or malignant course. "Melanocytic lesion" encompasses both benign melanocytic neoplasms, such as "nevi" and "lentigines" and "melanocytomas"; malignant melanocytic neoplasms, and "melanoma" and "malignant blue nevus".

The terms "tumor" or "cancer" in an animal refers to the presence of cells possessing characteristics such as atypical growth or morphology, including uncontrolled proliferation, immortality, metastatic potential, rapid growth and proliferation rate, and certain characteristic morphological features. Often, cancer cells will be in the form of a tumor, but such cells may exist alone within an animal. "Tumor" includes both benign and malignant neoplasms. The term "neoplastic" refers to both benign and malignant atypical growth.

The terms "hybridizing specifically to", "specific hybridization", and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. An extensive guide to the hybridization of nucleic acids is found in, e.g., Tijssen (1993) *Laboratory Techniques in Biochemistry and Molecular Biology—Hybridization with Nucleic Acid Probes part I, Ch. 2, "Overview of principles of hybridization and the strategy of nucleic acid probe assays,"* Elsevier, N.Y. ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook and Russell (2001) *Molecular Cloning: A Laboratory Manual* (3rd ed.) Vol. 1-3, Cold Spring Harbor Laboratory, Cold Spring Harbor Press, NY, and detailed discussion, below).

The term "nucleic acid" as used herein refers to a deoxyribonucleotide or ribonucleotide in either single- or double-stranded form. The term encompasses nucleic acids, i.e., oligonucleotides, containing known analogues of natural nucleotides which have similar or improved binding properties, for the purposes desired, as the reference nucleic acid. The term also includes nucleic acids which are metabolized in a manner similar to naturally occurring nucleotides or at rates that are improved for the purposes desired. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl)glycine units. Phosphorothioate linkages are described in WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (Strauss-Soukup (1997) Biochemistry 36: 8692-8698), and benzylphosphonate linkages (Samstag (1996) Antisense Nucleic Acid Drug Dev 6: 153-156). The term nucleic acid is used interchangeably with gene, cDNA, mRNA, oligonucleotide primer, probe and amplification product.

The term "biological sample" or "specimen" is intended to mean a sample obtained from a patient suspected of having, or having melanoma. Typically, the sample comprises a formalin-fixed paraffin-embedded skin biopsy of a body region suspected to contain melanoma cells. In addition to patients suspected of having melanoma, the biological sample may further be derived from a subject that has been diagnosed with melanoma for confirmation of diagnosis or establishing that all of the tumor was removed ("clear margin"). In addition, the biological sample may be derived from non-skin tissue such as lymph nodes to establish whether any melanocytes present in this tissue represent melanoma or nevus. The biological sample may be derived from a subject with an ambiguous diagnosis in order to clarify the diagnosis. The sample may be derived from a "punch", "shave", curettage, fine needle aspirate, sentinel lymph node or excisional biopsy, or other excision of the region including the suspected lesion or peripheral to the suspected or known lesion in order to establish a clear margin.

"Tissue biopsy" refers to the removal of a biological sample for diagnostic analysis. In a patient with cancer, tissue may be removed from a tumor, allowing the analysis of cells within the tumor.

The terms "nucleic acid sample" or "sample of human nucleic acid" as used herein refers to a sample comprising human DNA or RNA in a form suitable for detection by hybridization or amplification. For example, such a sample can be prepared from a skin tissue sample of a tumor from a patient who has or is suspected of having a melanocytic tumor that may be difficult to classify.

The term "probe" or "nucleic acid probe", as used herein, is defined to be a collection of one or more nucleic acid fragments whose specific hybridization to a nucleic acid sample comprising a regions of interest can be detected. The probe may be unlabeled or labeled as described below so that its binding to the target nucleic acid of interest can be detected.

What "probe" refers to specifically is clear from the context in which the word is used. The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854). One of skill will recognize that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived (see discussion above). Such modifications are specifically covered by reference to the individual probes described herein.

The term "target region" or "nucleic acid target" refers to a nucleotide sequence that resides at a specific chromosomal location whose loss and/or gain is indicative of the presence of melanoma. The "target region" or "nucleic acid target" is specifically recognized by a probe.

"Providing a nucleic acid sample" means to obtain a biological sample for use in the methods described in this invention. Most often, this will be done by removing a sample of cells from an animal, but can also be accomplished by using previously isolated cells (e.g. isolated by another person).

Chromosomal Regions for the Detection of Melanoma

The present invention provides methods detecting melanoma where the methods comprise detecting various chromosome subregions. The methods thus comprises detecting a gain of chromosome 1q21, 1q32, 1q42-43, 5p13-5p15, 6p24-6p21, 7q35-7q36, or 12q15. In other embodiments, the methods comprise detecting a loss of 9pter-9p24, 10q21-10q22, 10q23.3-10q24.1 (from about 89,698,198 to about 93,052,778), 10q25-10q26, or 21q21.

In some embodiments, changes in the chromosomal regions depicted in Table 1 are detected. These include a gain of 1q21, 1q32, 1q42, 5p15, 6p22-6p24, 6p21, 7q36, or 12q15. In other embodiments, the change in copy number is a loss of 9p24, 10q21, 10q23.3-10q24.1 (from about 89,698,198 to about 93,052,778), 10q25, 21q21. As appreciated by one of skill in the art, any number of probes can be used to detect the chromosomal region of interest. The following provides examples of probes that can be used to detect the regions shown in Table 1. The sizes of the regions shown in column 1 of Table 1 (the approximate base ranges encompassed by the regions) are as determined according to July 2003 release of the Genome Browser of the University of California, Santa Cruz. The last column of Table 1 shows the OMIM accession number).

1q21: Any probe that detects an increase in copy number at 1q21, e.g., a probe that selectively hybridizes to sequences within region 1q21, can be used to detect melanoma. For example, a probe can be selected that hybridizes to 1q21.1, 1q21.2, or 1q21.3. Further, a probe that detects a gene of interest can be used to evaluate copy number. Thus, in some embodiments, a probe, e.g., a probe that selectively hybridizes to the gene of interest, can be used to detect an increase in copy number of BCL9, MCL1, or CTSK. In other embodiments, a probe(s) that detects an increase in copy number of 1q21 can hybridize to any region of chromosome 1 from about 143,222,844 to about 148,581,317.

1q32: Any probe that detects an increase in copy number at 1q32, e.g., a probe that selectively hybridizes to sequences within region 1q32, can be used to detect melanoma. For example, a probe can be selected that hybridizes to 1q32.1.

Further, a probe that detects a gene of interest can be used to evaluate copy number. Thus, in some embodiments, a probe, e.g., a probe that selectively hybridizes to the gene of interest, can be used to detect an increase in copy number of MDM4, GAC1, IKBKE, RASSF5, MAPKAPK2, or TOSO. In other embodiments, a probe(s) that detects an increase in copy number of 1q32 can hybridize to any region of chromosome 1 from about 199,789,307 to about 204,974,194.

6p24-6p22: Any probe that detects an increase in copy number at chromosome region 6p22-6p24, e.g., a probe that selectively hybridizes to sequences within region 6p22-6p24, can be used to detect melanoma. For example, a probe can be selected that hybridizes to 6p24.1, 6p24.2, 6p24.3, 6p23, or 6p22.3. Further, a probe that detects a gene of interest can be used to evaluate copy number. Thus, in some embodiments, a probe, e.g., a probe that selectively hybridizes to the gene of interest, can be used to detect an increase in copy number of GCNT2, NEDD9, or RANBP9. In other embodiments, a probe(s) that detects an increase in copy number of 6p24-6p22 can hybridize to any region of chromosome 6 from about 10,487,688 to about 15,628,540.

16p21: Any probe that detects an increase at chromosome region 6p21, e.g., a probe that selectively hybridizes to sequences within region 6p21, can be used to detect melanoma. For example, a probe can be selected that hybridizes to 6p21.1, 6p21.2, 6p21.3, such as 6p21.31. Further, a probe that detects a gene of interest can be used to evaluate copy number. Thus, in some embodiments, a probe, e.g., a probe that selectively hybridizes to the gene of interest, can be used to detect an increase in copy number of STK38, PIM1, TFEB, FRS3, C6orf49, CCND3, PTK7, PARC, or VEGF. In other embodiments, a probe(s) that detects an increase in copy number of 6p21 can hybridize to any region of chromosome 6 from about 36,380,827 to about 43,801,031.

9p24: Any probe that detects a decrease in copy number at chromosome region 9p24, e.g., a probe that selectively hybridizes to sequences within region 9p24, can be used to detect melanoma. For example, a probe can be selected that hybridizes to 9p24.3, 9p24.2, or 9p24.1. Further, a probe that detects a gene of interest can be used to evaluate copy number. Thus, in some embodiments, a probe, e.g., a probe that selectively hybridizes to the gene of interest, can be used to detect a decrease in copy number of KANK, SMARCA2, JAK2, PDCD1L1, PDL2, NIRF, or PTPRD. In other embodiments, a probe(s) that detects a decrease in copy number of 9p24 can hybridize to any region of chromosome 9 from about 666,890 to about 9,008,737.

10q21: Any probe that detects a decrease in copy number at chromosome region 10q21, e.g., a probe that selectively hybridizes to sequences within region 10q21, can be used to detect melanoma. For example, a probe can be selected that hybridizes to 10q21.1. Further, a probe that detects a gene of interest can be used to evaluate copy number. Thus, in some embodiments, a probe, e.g., a probe that selectively hybridizes to the gene of interest, can be used to detect a decrease in copy number of DKK1, PCDH15, or ZWINT. In other embodiments, a probe(s) that detects a decrease in copy number of 10q21 can hybridize to any region of chromosome 10 from about 52,296,604 to about 59,453,954.

10q25: Any probe that detects a decrease in copy number at chromosome region 10q25, e.g., a probe that selectively hybridizes to sequences within region 10q25, can be used to detect melanoma. For example, a probe can be selected that hybridizes to 10q25.2. Further, a probe that detects a gene of interest can be used to evaluate copy number. Thus, in some embodiments, a probe, e.g., a probe that selectively hybridizes to the gene of interest, can be used to detect a decrease in copy number of MXI1 or SHOC2. In other embodiments, a probe(s) that detects a decrease in copy number of 10q25 can hybridize to any region of chromosome 10 from about 111,543,766 to about 114,186,345.

1q42: Any probe that detects an increase in copy number at 1q42, e.g., a probe that selectively hybridizes to sequences within region 1q42, can be used to detect melanoma. For example, a probe can be selected that hybridizes to 1q42.3. Further, a probe that detects a gene of interest can be used to evaluate copy number. Thus, in some embodiments, a probe, e.g., a probe that selectively hybridizes to the gene of interest, can be used to detect an increase in copy number of RBP1L1. In other embodiments, a probe(s) that detects an increase in copy number of 1q42 can hybridize to any region of chromosome 1 from about 229,578,925 to about 233,669,920.

5p15: Any probe that detects an increase in copy number at 5p15, e.g., a probe that selectively hybridizes to sequences within region 5p15, can be used to detect melanoma. For example, a probe can be selected that hybridizes to 5p15.2. Further, a probe that detects a gene of interest can be used to evaluate copy number. Thus, in some embodiments, a probe, e.g., a probe that selectively hybridizes to the gene of interest, can be used to detect an increase in copy number of CTNND2. In other embodiments, a probe(s) that detects an increase in copy number of 5p15 can hybridize to any region of chromosome 5 from about 11,435,334 to about 15,107,920.

7q36: Any probe that detects an increase in copy number at 7q36, e.g., a probe that selectively hybridizes to sequences within region 7q36, can be used to detect melanoma. For example, a probe can be selected that hybridizes to 7q36.2 or 7q36.3. Further, a probe that detects a gene of interest can be used to evaluate copy number. Thus, in some embodiments, a probe, e.g., a probe that selectively hybridizes to the gene of interest, can be used to detect an increase in copy number of PAXIP1L, EN2, SHH, HLXB9, or DNAJB6. In other embodiments, a probe(s) that detects an increase in copy number of 7q36 can hybridize to any region of chromosome 7 from about 153,599,469 to about 157,964,369.

12q15: Any probe that detects an increase in copy number at 12q15, e.g., a probe that selectively hybridizes to sequences within region 12q15, can be used to detect melanoma. Further, a probe that detects a gene of interest can be used to evaluate copy number. Thus, in some embodiments, a probe, e.g., a probe that selectively hybridizes to the gene of interest, can be used to detect an increase in copy number of RAP1B, MDM2, GAS41, or FRS2. In other embodiments, a probe(s) that detects an increase in copy number of 12q15 can hybridize to any region of chromosome 12 from about 66,705,893 to about 74,222,988.

21q21: Any probe that detects a decrease in copy number at chromosome region 21q21, e.g., a probe that selectively hybridizes to sequences within region 21q21, can be used to detect melanoma. For example, a probe can be selected that hybridizes to 21q21.1. Further, a probe that detects a gene of interest can be used to evaluate copy number. Thus, in some embodiments, a probe, e.g., a probe that selectively hybridizes to the gene of interest, can be used to detect a decrease in copy number of NCAM2 or BC009878. In other embodiments, a probe(s) that detects a decrease in copy number of 21q21 can hybridize to any region of chromosome 21 from about 21,292,504 to about 22,017,484.

10q23.3-10q24.1: In the current invention, a probe for the detection of a decrease in copy number at 10q23.3-10q24 hybridizes to a region of chromosome 10. The region of 10q23.3 is from about 89,698,198 to about 93,052,778 as shown in Table 1. This region for the purposes of this application excludes the PTEN gene. A probe that detects a gene of interest, such as a gene in Table 1, can be used to evaluate copy number. Thus, in some embodiments, a probe, e.g., a probe that selectively hybridizes to the gene of interest, can be used to detect a decrease in copy number of FAS, ANKRD22, STAMPBL, ACTA2 LIPA, IFIT2, IFIT3, IFIT1L, IFIT1, IFIT5, MPHOSPH1, HTR7, RPP30, or ANKRD1.

A probe to a chromosomal region can include one or more polynucleotides that specifically hybridize to a region of a chromosome. The target sequences to which the probe can bind vary in length, typically the target size is from about 70,000 nucleotides to about 800,000 nucleotides. Smaller probes, e.g., that hybridize to a region of less than 100,000 nucleotides; or to a region of less than 10,000 nucleotides, can also be employed. As understood in the art, the size of the probe can vary, depending on the method employed for detecting copy number change.

A probe to a particular chromosomal region can comprise multiple polynucleotide fragments, e.g., ranging in size from about 50 to about 1,000 nucleotides in length.

Gains or losses are typically considered to be present in a given sample if a considerable proportion of the constituent tumors cells (e.g., >20%) show copy numbers above or below the numbers of copies expected by the ploidy of the tumor. For example, in a diploid cell, copy numbers below 2 would be considered losses, and copy numbers above 2 gains. In a tetraploid cell, copy numbers below 4 would be considered losses, and copy numbers above 4 would be considered gains. In a FISH-based assay, ploidy is usually inferred by comparing the number of signals of the probe of interest to a different probe, e.g. one that targets a region in the genome not frequently affected by copy number changes or the centromere of the same chromosome targeted by the probe of interest. In CGH based assays gains and losses are defined by comparing the ratios of the fluorescence intensity of the tumor DNA to that of the reference DNA.

Detection of Copy Number Changes

There are numerous techniques for detecting copy number changes that are well known in the art. For example, fluorescence in-situ hybridization (FISH) can be used to study copy numbers of individual genetic loci or particular regions on a chromosome (Pinkel et al., *Proc. Natl. Acad. Sci. U.S.A.* 85, 9138-42 (1988)). Comparative genomic hybridization (CGH) (Kallioniemi et al. *Science* 258, 818-21 (1992)) may also be used (Houldsworth et al. *Am J Pathol* 145, 1253-60 (1994)) to probe for copy number changes of chromosomal regions as well as changes in chromosome number. In other embodiments, amplification techniques, e.g., quantitative PCR, southern blotting, dot blotting or other techniques can be employed to determine copy number and copy number changes.

The nucleic acid sample that is analyzed for copy number is often be a tissue or cell sample prepared for hybridization using methods described below. The sample is prepared such that individual chromosomes remain substantially intact according to standard techniques. Alternatively, the nucleic acid may be isolated, cloned or amplified. It may be, e.g., genomic DNA, mRNA, or cDNA from a particular chromosome, or selected sequences (e.g. particular promoters, genes, amplification or restriction fragments, cDNA, etc.) within particular amplicons or deletions disclosed here. In some cases, the nucleic acids may be amplified using standard techniques such as PCR. The sample may be isolated nucleic acids immobilized on a solid.

The nucleic acid sample is typically extracted from particular cells, e.g. melanocytes, or prepared from a skin tumor, i.e., a melanocytic neoplasm. Methods of isolating cell and tissue samples are well known to those of skill in the art and include, but are not limited to, aspirations, tissue sections, needle biopsies, and the like. Frequently the sample will be a "clinical sample" which is a sample derived from a patient, including sections of tissues such as frozen sections or paraffin sections taken for histological purposes. The sample can also be derived from extracts or supernatants from the cells or the cells themselves from cell cultures, cells from tissue culture and other media in which it may be desirable to detect chromosomal abnormalities, such as changes in copy number. In some cases, the nucleic acids may be amplified using standard techniques such as PCR, prior to the hybridization. The sample may be isolated nucleic acids immobilized on a solid.

As appreciated by one of skill in the art, analysis of copy number can be performed using multiple probes to a particular chromosome region or using a single probe to detect change in copy number. Probes useful in the methods described here are available from a number of sources. For instance, P1 clones are available from the DuPont P1 library (Shepard, et al., *Proc. Natl. Acad. Sci. USA*, 92: 2629 (1994), and available commercially from Genome Systems. Various libraries spanning entire chromosomes are also available commercially (Clontech, South San Francisco, Calif.), or from the Los Alamos National Laboratory.

In one set of embodiments, the hybridizations are performed on a solid support. For example, probes that selectively hybridize to specific chromosomal regions can be spotted onto a surface in an array. Embodiments include chips or microfluidic devices.

Alternatively, the samples can be placed in separate wells or chambers and hybridized in their respective well or chambers. The art has developed robotic equipment permitting the automated delivery of reagents to separate reaction chambers, including "chip" and microfluidic techniques, which allow the amount of the reagents used per reaction to be sharply reduced. Chip and microfluidic techniques are taught in, for example, U.S. Pat. No. 5,800,690, Orchid, "Running on Parallel Lines" New Scientist, Oct. 25, 1997, McCormick, et al., *Anal. Chem.* 69:2626-30 (1997), and Turgeon, "The Lab of the Future on CD-ROM?" *Medical Laboratory Management Report*. December 1997, p. 1. Automated hybridizations on chips or in a microfluidic environment are contemplated methods of practicing the invention.

In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained.

The probes are typically labeled, e.g., with radioisotopes or fluorescent reporters. The preferred size range is from about 200 bp to about 1000 bases, more preferably between about 400 to about 800 bp for double stranded, nick translated nucleic acids.

In some applications it is necessary to block the hybridization capacity of repetitive sequences. Thus, in some embodiments, human genomic DNA or Cot-1 DNA is used to block non-specific hybridization.

CGH methods a sample nucleic acid from a biological sample is labeled with a first label, while a second collection of control nucleic acids (e.g. from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number.

Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology, Vol.* 33. *In Situ Hybridization Protocols*, Choo, ed., Humana Press, Totowa, N.J. (1994), etc. In some embodiments, the hybridization protocol of Pinkel et al. (1998) *Nature Genetics* 20:207-211 or of Kallioniemi (1992) *Proc. Natl. Acad Sci USA* 89:5321-5325 (1992) is often used.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

Background signal can be reduced, e.g., by the use of a detergent or a blocking reagent (e.g., sperm DNA, cot-1 DNA, etc.) during the hybridization to reduce non-specific binding. The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology, Vol.* 24: *Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background membranes can be used (see, e.g., Chu (1992) *Electrophoresis* 13:105-114). The sensitivity for detection of spots ("target elements") of various diameters on the candidate membranes can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., membranes, glass, fused silica) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

Other nucleic acid hybridization formats are also known to those skilled in the art. Such formats are described, for example in Sambrook and Russell, supra. These includes analyses such as southern blotting and dot blot analysis. The sensitivity of the hybridization assays may also be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

Chromosome number may also be determined using quantitative PCR such as real-time PCR (see, e.g., Suzuki et al., *Cancer Res.* 60:5405-9 (2000)). For example, quantitative microsatellite analysis (QuMA) can be performed for rapid measurement of relative DNA sequence copy number. In QuMA, the copy number of a test locus relative to a pooled reference is assessed using quantitative, real-time PCR amplification of loci carrying simple sequence repeats. Use of simple sequence repeats is advantageous because of the large numbers that are mapped precisely.

Additional protocols for quantitative PCR are provided in Innis et al. (1990) PCR Protocols, A Guide to Methods and Applications, Academic Press, Inc. N.Y.).

Probe Hybridization

Conditions for specifically hybridizing the probes to their nucleic acid targets generally include the combinations of conditions that are employable in a given hybridization procedure to produce specific hybrids, the conditions of which may easily be determined by one of skill in the art. Such conditions typically involve controlled temperature, liquid phase, and contact between a chromosomal probe and a target. Hybridization conditions vary depending upon many factors including probe concentration, target length, target and probe G-C content, solvent composition, temperature, and duration of incubation. At least one denaturation step must precede contact of the probes with the targets. Alternatively, both the probe and nucleic acid target may be subjected to denaturing conditions together while in contact with one another, or with subsequent contact of the probe with the biological sample. Hybridization may be achieved with subsequent incubation of the probe/sample in, for example, a liquid phase of about a 50:50 volume ratio mixture of 2-4× SSC and formamide, at a temperature in the range of about 25 to about 55° C. for a time that is illustratively in the range of about 0.5 to about 96 hours, or more preferably at a temperature of about 32 to about 40° C. for a time in the range of about 2 to about 16 hours. In order to increase specificity, use of a blocking agent such as unlabeled blocking nucleic acid as described in U.S. Pat. No. 5,756,696, the contents of which are herein incorporated by reference, may be used in conjunction with the methods of the present invention. Other conditions may be readily employed for specifically hybridizing the probes to their nucleic acid targets present in the sample, as would be readily apparent to one of skill in the art.

Upon completion of a suitable incubation period, non-specific binding of chromosomal probes to sample DNA may be removed by a series of washes. Temperature and salt concentrations are suitably chosen for a desired stringency. The level of stringency required depends on the complexity of a specific probe sequence in relation to the genomic sequence, and may be determined by systematically hybridizing probes to samples of known genetic composition. In general, high stringency washes may be carried out at a temperature in the range of about 65 to about 80° C. with about 0.2× to about 2×SSC and about 0.1% to about 1% of a non-ionic detergent such as Nonidet P-40 (NP40). If lower stringency washes are required, the washes may be carried out at a lower temperature with an increased concentration of salt.

Detection of Probe Hybridization

The hybridized nucleic acids are typically detected by detecting one or more labels attached to the sample or probe nucleic acids. The labels may be incorporated by any of a number of means well known to those of skill in the art. Means of attaching labels to nucleic acids include, for example nick translation or end-labeling (e.g. with a labeled RNA) by kinasing of the nucleic acid and subsequent attachment (ligation) of a nucleic acid linker joining the sample nucleic acid to a label (e.g., a fluorophore). A wide variety of linkers for the attachment of labels to nucleic acids are also known. In addition, intercalating dyes and fluorescent nucleotides can also be used.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like, see, e.g., Molecular Probes, Eugene, Oreg., USA), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

A fluorescent label is used in some embodiments because it provides a very strong signal with low background. It is also optically detectable at high resolution and sensitivity through a quick scanning procedure. The nucleic acid samples can all be labeled with a single label, e.g., a single fluorescent label. Alternatively, in another embodiment, different nucleic acid samples can be simultaneously hybridized where each nucleic acid sample has a different label. For instance, one target could have a green fluorescent label and a second target could have a red fluorescent label. The scanning step will distinguish cites of binding of the red label from those binding the green fluorescent label. Each nucleic acid sample (target nucleic acid) can be analyzed independently from one another.

Suitable chromogens which can be employed include those molecules and compounds which absorb light in a distinctive range of wavelengths so that a color can be observed or, alternatively, which emit light when irradiated with radiation of a particular wave length or wave length range, e.g., fluorescers.

Detectable signal can also be provided by chemiluminescent and bioluminescent sources. Chemiluminescent sources include a compound which becomes electronically excited by a chemical reaction and can then emit light which serves as the detectable signal or donates energy to a fluorescent acceptor. Alternatively, luciferins can be used in conjunction with luciferase or lucigenins to provide bioluminescence. Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. The nucleic acid probe may also be labeled with digoxigenin and then detected with an antibody that is labeled with a fluorochrome, or an enzyme such as horseradish peroxidase or alkaline phosphatase. For a detailed review of methods of labeling nucleic acids and detecting labeled hybridized nucleic acids see *Laboratory Techniques in Biochemistry and Molecular Biology, Vol.* 24: *Hybridization With Nucleic Acid Probes*, P. Tijssen, ed. Elsevier, N.Y., (1993)).

Fluorescent labels are easily added during an in vitro transcription reaction. Thus, for example, fluorescein labeled UTP and CTP can be incorporated into the RNA produced in an in vitro transcription.

The labels can be attached directly or through a linker moiety. In general, the site of label or linker-label attachment is not limited to any specific position. For example, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. As shown for example herein, labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

It will be recognized that fluorescent labels are not to be limited to single species organic molecules, but include inorganic molecules, multi-molecular mixtures of organic and/or inorganic molecules, crystals, heteropolymers, and the like. Thus, for example, CdSe—CdS core-shell nanocrystals enclosed in a silica shell can be easily derivatized for coupling to a biological molecule (Bruchez et al. (1998) *Science,* 281: 2013-2016). Similarly, highly fluorescent quantum dots (zinc sulfide-capped cadmium selenide) have been covalently coupled to biomolecules for use in ultrasensitive biological detection (Warren and Nie (1998) *Science,* 281: 2016-2018).

Detection of Changes in Gene Expression

In some embodiments, changes in gene expression are used to detect melanoma. For example, genes shown in Table 1 that are present in chromosomal regions that are increased or decreased copy number in melanoma can be evaluated for an increased or decreased, respectively, level of mRNA or protein encoded by the gene to detect melanoma. Accordingly, the present invention also provides for methods of detecting expression of the genes listed in Table 1, including expression of mRNAs or proteins encoded by the genes.

In one embodiment, the presence of melanoma is evaluated by determining the level of expression of mRNA encoding a protein of interest. Samples that are evaluated for mRNA levels can be from any biological source, including e.g., tissue biopsies. Methods of evaluating RNA expression of a particular gene are well known to those of skill in the art, and include, inter alia, hybridization and amplification based assays. For example, RNA levels can be analyzed by northern blot, dot blotting, in situ hybridization, RNase protection, probing DNA microchip arrays, and the like. Probes for such analyses can readily be obtained based on the known sequences of the indicated genes.

In other embodiments, amplification-based assays are used to measure the expression level of a gene of interest. Methods of quantitative amplification are known in the art and include such assays as quantitative PCR analyses. Again, the known nucleic acid sequences for the genes listed in Table 1 are sufficient to enable one of skill to routinely select primers for amplification of the gene of interest. Other suitable amplification methods include, but are not limited to, ligase chain reaction (LCR) (see, Wu and Wallace (1989) *Genomics* 4: 560, Landegren et al. (1988) *Science* 241: 1077, and Barringer et al. (1990) *Gene* 89: 117), transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.

In some embodiments, detection of melanoma is performed by analyzing levels of polypeptides encoded by a gene of interest, e.g., a gene listed in Table 1. The polypeptides can be detected and/or quantified by any methods known to those of skill in the art. Often, an antibody to a protein encoded by a gene of interest is employed in an immunological assay. For a review of immunological and immunoassay procedures, see *Basic and Clinical Immunology* (Stites & Terr eds., 7th ed. 1991).

In other embodiments, the level of protein can be determined by assessing the activity of the protein. Protein activity for the genes encoded by the proteins listed in Table 1 can be measured using methods for each protein that are known in the art.

The presence or an increase or decrease in RNA or protein level is determined relative to a normal control, e.g., a corresponding biological sample from an individual that does not have melanoma; or a biological sample obtained from a portion of tissue from the patient that is free of melanoma. An RNA or protein that is considered to be increased in level relative to a normal control often has at least 110%, more often at least 125%, 150%, or 200% or greater amount of mRNA or protein. An RNA or protein that is considered to be decreased in level relative to normal often has at least 90%, more often at least 75%, or 50%, or less of the amount of mRNA or protein compared to a normal control.

Kits for Use in Diagnostic and/or Prognostic Applications

Kits for use in diagnostic, research, and prognostic applications are also provided by the invention. Such kits may include any or all of the following: assay reagents, buffers, nucleic acids for detecting the target sequences and other hybridization probes and/or primers. The kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Screening and Diagnosis of Patients for Melanoma

The detection methods of the invention comprise obtaining a biological sample from a subject having melanoma or suspected of having melanoma. The biological sample is typically a tissue sample that comprises the melanocytic lesion. Often, the biological sample is formalin-fixed and paraffin embedded. The sample is contacted with one or more chromosomal probes to selectively detect melanoma in the sample, if any, under conditions for specifically hybridizing the probes to their nucleic acid targets present in the sample.

The biological sample can be from a patient suspected of having melanoma or from a patient diagnosed with melanoma, e.g., for confirmation of diagnosis or establishing a clear margin, or for the detection of melanoma cells in other tissues such as lymph nodes. The biological sample can also be from a subject with an ambiguous diagnosis in order to clarify the diagnosis. The biological sample can also be from a subject with a histopathologically benign lesion to confirm the diagnosis. Biological samples can be obtained using any of a number of methods in the art. Examples of biological samples comprising potential melanocytic lesions include those obtained from excised skin biopsies, such as punch biopsies, shave biopsies, fine needle aspirates, or surgical excisions; or biopsy from non-cutaneous tissues such as lymph node tissue, mucosa, meninx, conjuctiva, or uvea. In other embodiments, the biological sample can be obtained by shaving, waxing, or stripping the region of interest on the skin.

As noted, a biological sample can be treated with a fixative such as formaldehyde and embedded in paraffin and sectioned for use in the methods of the invention. Alternatively, fresh or frozen tissue can be pressed against glass slides to form monolayers of cells known as touch preparations, which contain intact nuclei and do not suffer from the truncation artifact of sectioning. These cells may be fixed, e.g., in alcoholic solutions such as 100% ethanol or 3:1 methanol:acetic acid. Nuclei can also be extracted from thick sections of paraffin-embedded specimens to reduce truncation artifacts and eliminate extraneous embedded material. Typically, biological samples, once obtained, are harvested and processed prior to hybridization using standard methods known in the art. Such processing typically includes protease treatment and additional fixation in an aldehyde solution such as formaldehyde.

Prescreening of Samples

Prior to detection, cell samples may be optionally pre-selected based on apparent cytologic abnormalities. Pre-selection identifies suspicious cells, thereby allowing the screening to be focused on those cells. Pre-selection allows for faster screening and increases the likelihood that a positive result will not be missed. During pre-selection, cells from a biological sample are placed on a microscope slide and visually scanned for cytologic abnormalities commonly associated with dysplastic and neoplastic cells. Such abnormalities include abnormalities in nuclear size, nuclear shape, and nuclear staining, as assessed by counterstaining nuclei with nucleic acid stains or dyes such as propidium iodide or 4,6-diamidino-2-phenylindole dihydrochloride (DAPI) usually following hybridization of probes to their target DNAs. Typically, neoplastic cells harbor nuclei that are enlarged, irregular in shape, and/or show a mottled staining pattern. In embodiments in which preselection is employed, only those cells pre-selected for detection are subjected to analysis for chromosomal losses and/or gains. Preferably, pre-selected cells on the order of at least 20, and more preferably at least 30-40, in number are chosen for assessing chromosomal losses and/or gains. Preselection of a suspicious region on a tissue section may be performed on a serial section stained by conventional means, such as H&E or PAP staining, and the suspect region marked by a pathologist or otherwise trained technician. The same region is then located on the serial section stained by FISH and nuclei enumerated within that region. Within the marked region, enumeration may be limited to nuclei exhibiting abnormal characteristics as described above.

Alternatively, cells for detection may be chosen independent of cytologic or histologic features. For example, all non-overlapping cells in a given area or areas on a microscope slide may be assessed for chromosomal losses and/or gains. As a further example, cells on the slide, e.g., cells that show altered morphology, on the order of at least about 50, and more preferably at least about 100, in number that appear in consecutive order on a microscope slide may be chosen for assessing chromosomal losses and/or gains.

Hybridization is detected by the presence or absence of the particular signals generated by a chromosomal probe. A gain or loss is determined by comparing the number of distinct probe signals in each cell to the number expected in a normal cell, i.e., where the copy number should be two. Non-neoplastic cells in the sample, such as keratinocytes, fibroblasts, and lymphocytes, can be used as reference normal cells. More than the normal number of probe signals is considered a gain, and fewer than the normal number is considered a loss. Alternatively, a minimum number of signals per probe per cell can be required to consider the cell abnormal (e.g., 5 or more signals). Likewise for loss, a maximum number of signals per probe can be required to consider the cell abnormal (e.g., 0 signals, or one or fewer signals).

The percentages of cells with at least one gain and/or loss can be recorded for each locus of interest. A cell is considered abnormal if at least one of the identified genetic aberrations identified by a probe to a chromosomal region described herein is found in that cell. A sample may be considered positive for a gain or loss if the percentage of cells with the respective gain or loss exceeds the cutoff value for any probes used in an assay. Alternatively, two or more genetic aberrations can be required in order to consider the cell abnormal with the effect of increasing specificity.

EXAMPLES

Material and Methods

Archival paraffin-embedded primary melanomas that had an invasive component in which tumor cells dominated over stroma cells were obtained from the Dermatopathology Section of the Department of Pathology and Dermatology, University of California, San Francisco; the Department of Dermatology, Kumamoto University School of Medicine, Kumamoto, Japan; the Department of Pathology, Memorial-Sloan-Kettering Cancer Center, New York, N.Y.; the Dermatohistopathologic Laboratory, Friedrichshafen, Germany; Department of Dermatology, Seoul National University College of Medicine, Seoul, Korea; the Department of Dermatology, Tohoku University School of Medicine, Sendai, Japan, and the Department of Dermatology, University of Würzburg, Germany. Tumors were selected to obtain four groups of comparable sizes: acral melanoma was defined as melanoma occurring on the nonhair-bearing skin of the palms or soles or under the nails (n=36); mucosal melanomas were defined as arising on mucosal membranes (n=20); the remainder of the specimens were divided into melanoma arising from chronically sun damaged skin (CSD; n=30) and melanoma arising from skin without chronic sun damage (non-CSD; n=40), a distinction based solely on the microscopic presence or absence of marked solar elastosis of the dermis surrounding the melanomas. In all but a few cases CSD melanoma occurred on the face, and non-CSD melanoma cases occurred on the trunk and extremities.

CGH: DNA was extracted from tumor bearing tissue as published previously 22 Array CGH hybridization was carried out on 600-2000 ng of genomic DNA, labeled by random priming, as previously described (Snijder et al., Oncogene 22:4370-4379, 2003). Data points with low quality, as assessed by high standard deviation between replicate spots on each array, were rejected. Clones that had missing data in more than 25% of the samples of the entire cohort or in 50% in any individual group were excluded from further analysis. The data set used for comparative genomic hybridization has been deposited in the Gene Expression Omnibus (accession number GSE2631).

Immunohistochemistry Immunohistochemistry was performed using standard protocols with 3-amino-9-ethylcarbazole as a chromagen following the manufacturer's specifications on tissue microarrays as previously described (Bastian et al., *Am. J. Pathol.* 157:967-972, 2000). The following antibodies were used: Cyclin D1, monoclonal antibody AM29 Cat #18-0220 (Zymed, South San Francisco, Calif., dilution 1:200) as described previously (Sauter et al., *Cancer Res.* 62:3200-3206, 2002); CDKN2A Ab-4 monoclonal antibody Cat #MS-887-P1 (Lab Vision Corporation, Freemont, Calif., dilution 1:25); Phospho-Akt (Ser473): polyclonal antibody Cat #9277S (Cell Signaling Technology, Inc., Beverly, Mass., dilution 1:80); Phospho-ERK (Thr202/Tyr204): E10 monoclonal antibody Cat #9106S (Cell Signaling Technology, Inc., dilution 1:80). Staining intensity levels were scored from 0-4. For statistical analysis expression levels of 2 and greater were considered positive.

Sequence analysis of BRAF codon 600 (113 cases) and codons 12, 13 and 61 of NRAS (113 cases), HRAS and KRAS (95 cases, respectively) was performed by direct sequencing of PCR amplified products generated with specific primers designed to include the codon of interest. PCR products were purified using ExoSAP-IT® (USB Corporation, Cleveland, Ohio) and sequenced directly using an ABI PRISM® 3700 DNA Analyzer (Applied Biosystems, Foster City, Calif.).

Statistical Methods The experimental variability of each array CGH sample was assessed as described previously (Fridlyand et al., *J. Multivariate Analysis* 90:132-153, 2004). For each hybridization, the median absolute deviation (MAD, a robust estimate of the standard deviation) was calculated for each portion of the genome found to be at constant copy number, and the median of those values was used to estimate the measurement noise level. Copy number transitions and whole chromosomal changes were determined by applying the unsupervised Hidden Markov Model procedure as previously described (Fridlyand, et al., 2004, supra) and used to assess overall genomic instability (Snijders, et al., *Oncogene* 2003; 22:4370-4379, 2003). Clones with absolute log 2 ratios greater than 2.5 times the MAD were classified as aberrant (gained or lost). The proportion of the genome altered for each sample was computed as the proportion of aberrant clones. Clones were declared homozygously lost if their log 2 ratio was less than −0.9. Definition of high-level amplification involved assessing the height of the copy number increase and the narrowness of the affected region relative to its flanking segments. Amplicons were defined as contiguous regions of amplification. Missing values were imputed using the lowess approach (Cleveland, *American Statistician* 35:54, 1981). The F-statistic, corrected for multiple testing using maxT-adjusted permutation-based p values, was used to assess the significance of ratio differences of individual clones among the melanoma groups (Westfall & Young, Resampling-Based Multiple Testing: Examples and Methods for p-Value Adjustment. New York: Wiley, 1993). Adjusted p-values of less than 0.05 were regarded as significant, insuring probability of at least one false discovery of no more than 0.05 and thus providing strong control of the family-wise error rate (FWER). We compared individual clones containing genes of interest between two or more groups using the Kruskal-Wallis Test. Significance of the 2×2 tables comparing mutation status or cluster assignments among melanoma groups was determined using Fisher's Exact Test. The misclassification rate of the classifiers was assessed using the leave-one-out cross-validation method by repeatedly applying a diagonal linear discriminant analysis classifier while varying the number of features used by the predictor (Dudoit et al., *J. Am. Statistical Assoc.* 2002; 97:77-87, 2002). Features were reselected at each cross-validation step using F-statistic ranking. Hence only samples in the most current training set were used, thus eliminating potential downward bias of the resulting error rate. The reported leave-one-out error-rates correspond to the predictor with the number of features resulting in the best performance of the classifier. All calculations were done in R statistical language (Ikaka & Gentleman, *J. Com. Graph. Statistics* 5:229-314.31, 1996).

Supplementary Information—CGH Statistical Analysis

Primary data processing: Image and data analysis using UCSF SPOT (Jain et al., *Genome Res.* 2002; 12:325-332, 2002). The arrays contain 2462 clones printed as triplicate spots. Ratios for each spot were calculated as the total background-corrected fluorescence intensity ratios for the test and reference channels. No other computational adjustments were applied to the data. SPROC software was used to automatically filter the data based on quality criteria, average the log 2 ratios of the replicate spots, and assign genome position. Only clones for which two or more spots passed quality criteria and for which the standard deviation of the replicates was less than 0.2 were included in the subsequent analysis. Data were normalized to set the median log 2 ratio to zero.

Prior to the statistical analysis, clones were removed if data were missing in more than 25% of the samples or in 50% of any individual melanoma sub-group. Only clones that were mapped on the genome sequence and which did not detect copy number polymorphisms in normal samples were used. For classification and genome-wide testing, missing values were imputed using the lowess approach (Cleveland, supra), which predicts missing values on a given profile using values observed on the neighboring clones via piecewise linear regression. The procedure was implemented in the aCGH package.

Definition of aberrations: A clone was declared aberrant if its absolute value exceeded the tumor specific threshold computed as 2.5 times the estimate of the standard deviation of the experimental noise for a given profile (Fridlyand et al., 2004, supra). Amplifications were detected using the default parameters of the aCGH package, which implements the algorithm described in Fridlyand et al (2004, supra). A clone was considered amplified if it belonged to a narrow region with sufficiently higher log 2 ratio compared to its neighbors. Specifically, the algorithm identifies regions, which are smaller than 10 Mbases and whose absolute log 2 ratio exceeds 0.9 and also exceed the log 2 ratio of its immediately flanking regions by at least 0.5. The algorithm also identifies regions narrower than 10 Mbases whose log 2 ratios exceed immediately flanking segments by 0.9. The latter rule permits the detection of amplifications originating out of regions present at decreased copy number. Clones with log 2 ratios less than −0.9 were considered homozygously deleted. These levels were chosen empirically due to the expected presence of normal cells in the specimens and tumor heterogeneity and are concordant with the thresholds used in previously published array CGH articles (Mehta et al., *Clin Cancer Res.* 11: 1791-1797, 2005; Nakao et al., *Carcinogenesis* 25:1345-1357, 2004).

Classification: For all classification procedures, the DLDA prediction rule (Dudoit, supra, Linear Discriminant Analysis with covariance matrix identical for all groups and with zero-off-diagonal elements) was used and the grid of the number of variables (10 through 1000) was set. Each sample was repeatedly left out the entire classification procedure (including variable selection using an F-statistic and mean and covariance matrix estimation) and for a given number of variables the predictor was built using the remaining samples. The left-out sample was predicted using the resulting classifier. The procedure was repeated for all samples and all variables in a grid. The leave-one-out error rate was stable across a wide range of variables (at least 200 variables for 2-class problems and at least 400 variables for 4-class problem)

Results

Array CGH found several genomic regions to be commonly affected by copy number changes in all four groups (FIG. 1). In addition, there were differences in aberrant genomic regions between the groups (FIG. 1 and Table 2), as some of the regions identified were more commonly changed in copy number in particular types of melanomas. Those regions are noted by bold font in the last column of Table 2.

The differences in aberrant genomic regions were most pronounced between melanomas from relatively or absolutely sun protected skin (acral and mucosal), and melanomas with varying degrees of sun-exposure (CSD and non-CSD). Specifically, melanomas on acral skin or mucosa showed a significantly higher degree of chromosomal aberrations as assessed by the overall proportion of the genome affected by gains or losses of DNA ($p=0.004$, Kruskal-Wallis Test), the number of copy number transitions within chromosomes ($p<0.001$, Kruskal-Wallis Test) and the number of amplicons ($p<0.001$ Kruskal-Wallis Test). Amplifications were found in 89% of acral melanomas and 85% of mucosal melanomas, but they involved different genomic regions in the two groups (FIG. 1 and Table 2). Amplifications were infrequent in the CSD and non-CSD groups. In addition to these differences in the degree of genomic instability there were differences in aberration patterns between the four groups. The last column in Table 2 shows common genomic aberrations and the regions that were affected with different frequencies in each group when adjusted for multiple testing. Based on the copy number changes alone, samples could be correctly classified into the four groups with 70% overall accuracy. Two-way classification of acral and mucosal melanomas correctly classified 50 out of 56 samples (89%). Further, two-way classification of non-CSD and CSD lead to correct classification of 59 out of 70 samples (84%). Unsupervised agglomerative hierarchical clustering separated CSD and non-CSD melanomas on sun-exposed skin into two major clusters ($p<0.001$, Fisher's Exact Test). Frequent focused gains of the cyclin D1 (CCND1) locus ($p=0.001$), losses involving 4q ($p=0.004$) and gains of 22 ($p=0.004$) were significantly more common in the CSD group than in the non-CSD group, which showed more frequent losses of 10q ($p=0.002$). All p-values were calculated using maxT adjusted permutation based t-test as described above and are reported for the most significant regions of the relevant chromosomes.

Alteration of the MAP-Kinase Pathway in Primary Melanoma

Mutations in BRAF were found significantly more commonly in non-CSD cases, whereas the other groups had fewer mutations ($p<0.001$, Fisher's Exact Test), as previously reported (*J. Natl. Cancer Inst.* 95:1878-1880, 2003). All mutations in RAS genes were found in NRAS and occurred only in samples without BRAF mutation. No significant association between NRAS mutations and melanoma subtypes (p=0.4, Fisher's Exact Test) was observed.

Immunohistochemistry analysis showed that, samples without mutations in BRAF or NRAS less frequently expressed phospho-ERK compared to samples with mutations, suggesting that in samples wild-type for BRAF and NRAS the pathway was not activated upstream of phospho-ERK. One downstream gene, CCND1, resided in the most common genomic region affected by focused amplifications. Copy number increases of CCND1 were inversely correlated with mutations in BRAF (p=0.008, Wilcoxon Rank-Sum Test), independent of the type of melanoma. Cases that showed increased expression levels of CCND1 by immunohistochemistry without exception either showed mutations in BRAF or NRAS or increased copy number of CCND1. His observation as well as the strong inverse correlation between BRAF mutations and CCND1 copy number increase, suggest that elevation of CCND1 levels either by mutations in upstream genes or increased gene dosage represents a crucial event driving melanoma progression.

One of the binding partners of CCND1, cyclin-dependent kinase 4 (CDK4) on chromosome 12q14 was also subject to recurrent focal amplifications. CDK4 amplifications were more common in acral and mucosal melanomas than in the other groups (p=0.005, Kruskal-Wallis Test). None of the 11 cases with CDK4 amplifications showed mutations in either BRAF or NRAS, or showed amplification of CCND1. The strong complementarity of the genetic interactions between CDK4, CCND1, BRAF, and RAS implicate CDK4 and CCND1 as independent oncogenes in melanoma.

The CDKN2A protein (also commonly known as p16) is a melanoma susceptibility factor and main negative regulator of the CDK4/CCND1 complex, representing a crucial gatekeeper at the G1/S checkpoint. In our investigation deletions of the CDKN2A locus were found in 50% of all melanomas, representing the most commonly lost genomic region. In 10% of our cases CGH indicated homozygous deletion of the CDKN2A locus paralleled by a complete loss of expression of CDKN2A protein by immunohistochemistry. Mucosal and acral melanomas had more common losses of the CDKN2A locus than melanomas in the CSD and non-CSD group (p<0.001, Kruskal-Wallis Test). Homozygous deletions of CDKN2A occurred exclusive of CDK4 amplifications. This observation suggests that amplification of CDK4 obviates the need for deletions of CDKN2A. As the CDKN2A and CDK4 proteins bind each other in a 1:1 ratio, tumor evolution in melanoma appears to favor decreasing the CDKN2A to CDK4 ratio in order to loosen checkpoint control for entry into S-phase. We did not note an influence of the tumor thickness on either the mutation frequencies of BRAF or RAS or on the amplification frequencies of cyclin D1 or CDK4 in the four groups of melanomas.

Alterations of the PI3-Kinase Pathway in Primary Melanoma

Several studies have implicated activation of the PI3-kinase pathway as another crucial event in melanoma progression. To date PTEN, a negative regulator of the pathway, appears to be the most common somatic target in melanoma, residing in a commonly deleted genomic area on 10q. In melanoma cell lines, mutations or deletions of PTEN occur together with mutations in BRAF, but not in NRAS. NRAS activates both the PI3-kinase and MAP-kinase pathway, whereas BRAF seems to activate only the latter, suggesting that during progression somatic events activating only one pathway require a second event to activate the other. Our data are consistent with this finding. Cases with BRAF mutations had significantly lower PTEN copy number than cases with NRAS mutations (p=0.02, Wilcoxon Rank-Sum Test). We confirmed activation of the PI3-kinase pathway by analyzing 51 cases with remaining tissue for expression of phospho-AKT by immunohistochemistry. In this subset of samples all 8 cases with NRAS mutations had increased phospho-AKT expression and 14 out of 17 cases (82%) with PTEN loss showed increased phospho-AKT expression. The positive correlation between PTEN loss and mutations in BRAF supports the notion that the PI3 kinase pathway is an independent somatic target that is frequently activated in primary melanoma.

Discussion

This study shows distinct patterns of genetic alterations in four groups of primary melanomas as we have defined them. These differences are seen both in genomic copy number aberrations and in the mutations of specific genes, suggesting that these tumors develop by different mechanistic routes in response to differing selective influences. For example, acral and mucosal melanomas were characterized by a higher frequency of focal amplifications and losses than the CSD and non-CSD tumors, indicating that the first two are mechanistically more similar to each other than to the other types. However, selection results in highly divergent sets of chromosomal aberrations in acral and mucosal tumors, supporting their classification as distinct entities. It was also found that clear genetic differences exist between the types of melanoma that commonly occur on sun-exposed areas of light-skinned individuals. For example, melanomas on skin without CSD had frequent mutations in BRAF and frequent losses of chromosome 10, whereas melanomas on skin with CSD had infrequent mutations in BRAF and frequent copy number increases of the CCND1 gene.

Knowledge of the genetic differences among melanomas is valuable in the design of therapeutic strategies. For example, tumors in the non-CSD group, which represent the most common type of melanoma, frequently showed mutation in BRAF together with loss of PTEN, or mutations in NRAS alone. Thus, they may be expected to be responsive to therapeutic intervention targeting the RAS/RAF/ERK and PI3-kinase pathways. In contrast, the majority of melanomas in the other three groups did not show mutations in BRAF or NRAS, but instead had copy number increases of the downstream genes CCND1 or CDK4. Thus these three latter groups of melanomas may be less likely to respond to therapeutic interventions targeting upstream components of the MAP-Kinase pathway including BRAF such as BAY 43-9006.

All publications, patents, accession numbers, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 1

| Region | | | | | | |
|---|---|---|---|---|---|---|
| Region 1 | Region searched on July3003 freeze of Golden Path: | | | | | |
| chr1: 143222844-148581317 | 143273737 | ITGA10 | 1q21.1 | integrin, alpha 10 | | 604042 |
| RP11-105E14 | 144520259 | BCL9 | 1q21.1 | B-cell CLL/lymphoma 9 | | 602597 |
| Gained in 45% of cases | 147020803 | HIST2H4 | 1q21.2 | histone 2, H4 | | 142750 |
| | | | | there are several other histone gene at this locus | | |
| | 147087783 | CGI-143 | 1q21.2 | CGI-143 protein | | |
| | 147131919 | ZA20D1 | 1q21.2 | zinc finger protein Cezanne | | |
| | 147763619 | MCL1 | 1q21.2 | myeloid cell leukemia sequence 1 isoform 1 | | 159552 |
| | 147985269 | CTSK | 1q21.2 | cathepsin K preproprotein | | 601105 |
| | 148154245 | LASS2 | 1q21.3 | LAG1 longevity assurance homolog 2 isoform 2 | | 606920 |
| | 148197555 | HTCD37 | 1q21.3 | TcD37 homolog | | |
| | 148225673 | BNIP-S | 1q21.3 | BNIP-Salpha | | |
| | 148249266 | AF1Q | 1q21.3 | AF1Q protein | | 604684 |
| Region 2 | Region searched on July3003 freeze of Golden Path: | | | | | |
| chr1: 199,789,307-204,974,19 | 199984790 | PLU-1 | 1q32.1 | putative DNA/chromatin binding motif | | |
| RP11-249H15 | 200562921 | BTG2 | 1q32.1 | B-cell translocation gene 2 | | |
| gained in 48% of cases | 201336903 | KiSS1 | 1q32.1 | KiSS-1 metastasis-suppressor | | |
| | 201552259 | PPP1R15B | 1q32.1 | protein phosphatase 1, regulatory (inhibitor) | | |
| | 201662999 | MDM4 | 1q32.1 | mouse double minute 4 homolog | | |
| | 201763736 | GAC1 | 1q32.1 | glioma amplified on chromosome 1 protein | | |
| | 202189861 | CNTN2 | 1q32.1 | contactin 2 precursor | | |
| | 202232709 | RBBP5 | 1q32.1 | retinoblastoma binding protein 5 | | |
| | | SNARK | | | | |
| | 202863848 | NUCKS | 1q32.1 | similar to rat nuclear ubiquitous casein kinase | | |
| | 202915112 | RAB7L1 | 1q32.1 | RAB7, member RAS oncogene family-like 1 | | 603949 |
| | 203727537 | IKBKE | 1q32.1 | IKK-related kinase epsilon | | 605048 |
| | 203764578 | RASSF5 | 1q32.1 | Ras association (RalGDS/AF-6) domain family 5 | | 607020 |
| | 203991325 | MAPKAPK2 | 1q32.1 | mitogen-activated protein kinase-activated | | 602006 |
| | 204161430 | TOSO | 1q32.1 | regulator of Fas-induced apoptosis | | 606015 |
| Region 3 | 10487688 | PAK1IP1 | 6p24.2 | PAK1 interacting protein 1 | | 607811 |
| Chr6: 10,487,688-15,628,540 | 10205047 | NT_007592.10 | 6p24.3 | | | |
| gained in 58% of samples | 10506385 | TFAP2A | 6p24.3 | transcription factor AP-2 alpha | | 107580 |
| | 10636575 | GCNT2 | 6p24.2 | I beta-1,6-N-acetylglucosaminyltransferase | | 600429 |
| | 11291520 | NEDD9 | 6p24.2 | neural precursor cell expressed, developmentally | | 602265 |
| | 11293381 | NT_007592.43 | 6p24.2 | | | |
| | 11436999 | NT_007592.44 | 6p24.2 | | | |
| | 12398645 | EDN1 | 6p24.1 | endothelin 1 | | 131240 |
| | 13730165 | RANBP9 | 6p23 | RAN binding protein 9 | | 603854 |
| | 15354506 | JMJ | 6p22.3 | jumonji | | 601594 |
| Region 4 | | | | | | |
| Chr6: 36,380,827-43,801,031 | | | | | | |
| CTD-2118F18 | 36380827 | ETV7 | 6p21.31 | Ets transcription factor TEL-2b | | 605255 |
| gained in 58% of samples | 36508525 | STK38 | 6p21.31 | serine/threonine kinase 38 | | 606964 |
| | 36609021 | SFRS3 | 6p21.31 | splicing factor, arginine/serine-rich 3 | | 603364 |
| | 36693342 | CDKN1A | 6p21.31 | cyclin-dependent kinase inhibitor 1A | | 116899 |
| | 37184841 | PIM1 | 6p21.2 | pim-1 oncogene | | 164960 |
| RP11-10M23 | 41561019 | FOXP4 | 6p21.1 | forkhead box P4 | | |
| gained in 45% of samples | 41698572 | TFEB | 6p21.1 | transcription factor EB | | 600744 |
| | 41784769 | FRS3 | 6p21.1 | fibroblast growth factor receptor substrate 3 | | 607744 |
| | 41795902 | C6orf49 | 6p21.1 | over-expressed breast tumor protein | | |
| | 41949527 | CCND3 | 6p21.1 | cyclin D3 | | 123834 |
| | 42999185 | PPP2R5D | 6p21.1 | delta isoform of regulatory subunit B56, protein | | 601646 |
| | 43090884 | PTK7 | 6p21.1 | PTK7 protein tyrosine kinase 7 isoform a | | 601890 |
| | 43198904 | PARC | 6p21.1 | p53-associated parkin-like cytoplasmic protein | | 607489 |
| | 43240224 | RCL | 6p21.1 | putative c-Myc-responsive | | |
| | 43350663 | ZNF318 | 6p21.1 | zinc finger protein 318 | | |
| | 43784801 | VEGF | 6p21.1 | vascular endothelial growth factor | | |
| Region 5 | Region searched on July3003 freeze of Golden Path: | | | | | |
| chr9: 666,890-9,008,737 | | | | | | |
| RP11-28N6:9p24:9:158 | 666890 | KANK | 9p24.3 | kidney ankyrin repeat-containing protein | | |
| loss on 48% of cases | 2005342 | SMARCA2 | 9p24.3 | SWI/SNF-related matrix-associated | | |
| RP11-12N24:9p24:9:5502 | 4975245 | JAK2 | 9p24.1 | Janus kinase 2 | | 147796 |
| loss in 42% of cases | 5440559 | PDCD1L1 | 9p24.1 | programmed cell death 1 ligand 1 | | |
| | 5500570 | PDL2 | 9p24.1 | programmed death ligand 2 | | 605723 |
| | 5880909 | MLANA | 9p24.1 | melan-A | | |
| RP11-264O11:9p23:9:11094 | 6,318,375 | NYD-SP25 | 9p24.1 | protein kinase NYD-SP25 | | |
| loss in 49% of cases | 6403151 | NIRF | 9p24.1 | Np95-like ring finger protein isoform a | | |
| RP11-32D4:9:12275:9p23 | 6748083 | GASC1 | 9p24.1 | gene amplified in squamous cell carcinoma 1 | | |
| loss in 46% of cases | 7466980 | NT_008413.148 | 9p24.1 | | | |
| RP11-58B8:9p23:9:12404 | 8307268 | PTPRD | 9p24.1 | protein tyrosine phosphatase, receptor type, D | | |
| loss in 43% of cases | | | | | | |
| Region 6 | | | | | | |
| chr10: 52,296,604-59,453,954 | | | | | | |
| RP11-67O23:10q21.1:10:558 | 53418681 | DKK1 | 10q21.1 | dickkopf homolog 1 | | |
| loss in 46% of cases | 54925463 | PCDH15 | 10q21.1 | protocadherin 15 precursor | | 605514 |
| | 57461810 | ZWINT | 10q21.1 | ZW10 interactor | | |

TABLE 1-continued

| Region / Locus | Position | Gene | Band | Description | ID |
|---|---|---|---|---|---|
| Region 7 | | | | | |
| chr10: 111,543,766-114,186,345 | | | | | |
| RP11-1I16:10q25:10:122610 | 111634576 | MXI1 | 10q25.2 | MAX interacting protein 1 isoform b | |
| loss in 48% of cases | 111992071 | CSPG6 | 10q25.2 | chondroitin sulfate proteoglycan 6 (bamacan) | |
| | 112296183 | PDCD4 | 10q25.2 | programmed cell death 4 isoform 2 | |
| | 112343960 | SHOC2 | 10q25.2 | soc-2 suppressor of clear homolog | |
| | 113854647 | ZDHHC6 | 10q25.2 | zinc finger, DHHC domain containing 6 | |
| Region 8 | | | | | |
| chr1: 229,578,925-233,669,920 | | | | | |
| RP11-155C15 | 232371361 | RBP1L1 | 1q42.3 | retinoblastoma binding protein 1-like 1 | |
| gained in 42% of cases | | | | | |
| Region 9 | | | | | |
| chr5: 11435334-15107920 | | | | | |
| CTD-2040C2 | 11025381 | CTNND2 | 5p15.2 | catenin (cadherin-associated protein), delta 2 | |
| gained in 31% of cases | | | | | |
| RP11-5N8 | | | | | |
| gained in 14% of cases | | | | | |
| Region 10 | | | | | |
| chr7: 153599469-157964369 | | | | | |
| GS1-121J16 | 154127141 | PAXIP1L | 7q36.2 | PAX transcription activation domain interacting | |
| gained in 42% of cases | 154666270 | EN2 | 7q36.3 | engrailed homolog 2 | |
| | 155012413 | SHH | 7q36.3 | sonic hedgehog preproprotein | |
| | 156215069 | HLXB9 | 7q36.3 | homeo box HB9 | |
| | 156546565 | DNAJB6 | 7q36.3 | DnaJ (Hsp40) homolog, subfamily B, member 6 | |
| Region 11 | | | | | |
| chr12: 66,705,893-74,222,988 | | | | | |
| | 67290991 | RAP1B | 12q15 | RAP1B, member of RAS oncogene family | 179530 |
| CTB-82N15 | 67488238 | MDM2 | 12q15 | mouse double minute 2 homolog full length | 164785 |
| gained in 20% of cases | 68039799 | GAS41 | 12q15 | glioma-amplified sequence-41 | 602116 |
| | 68150453 | FRS2 | 12q15 | suc1-associated neurotrophic factor target (FGFR | 607743 |
| Region 12 | | | | | |
| Chr 21: 21292504-22017484 | | | | | |
| loss in 49% of cases | 21292504 | NCAM2 | 21q21.1 | neural cell adhesion molecule 2 precursor | 602040 |
| loss in 59% of cases | 22017484 | BC009878 | 21q21.1 | tissue_type = "Skin, melanotic melanoma. | |
| Region 13 | | | | | |
| chr10: 89698198-93052778 | | | | | |
| loss in 37.39% of Cases | | | | | |
| | 89,698,198 | C10orf59 | 10q23.3 | Renalase precursor | |
| RP11-129G17 | 90,011,096 | LIPJ | 10q23.3 | LIPJ GC10P090337 lipase, family member J | |
| | 90,088,793 | LIPF | 10q23.3 | LIPF GC10P090415 lipase, gastric | |
| | 90,148,878 | LIPK | 10q23.3 | LIPK GC10P090476 lipase, family member K | |
| | 90,244,236 | ANKRD22 | 10q23.3 | Ankyrin repeat domain-containing protein 22 | |
| | 90,304,603 | STAMBPL1 | 10q23.3 | STAM binding protein-like 1 | |
| | 90,359,418 | ACTA2 | 10q23.3 | actin, alpha 2, smooth muscle, aorta | 102620 |
| | 90,414,865 | FAS | 10q23.3 | TNF receptor superfamily, member 6 FAS | |
| | 90,630,271 | CH25H | 10q23.3 | Cholesterol 25-Hydroxylase | |
| | 90,637,906 | LIPA | 10q23.3 | lipase A, lysosomal acid, cholesterol esterase | 278000 |
| | 90,726,380 | IFIT2 | 10q23.3 | interferon-induced protein with tetratricopeptide repeats 2 | |
| | 90,752,330 | IFIT3 | 10q23.3 | interferon-induced protein with tetratricopeptide repeats 3 | |
| | 90,802,390 | IFIT1L | 10q23.3 | Interferon-induced protein with tetratricopeptide repeats 1-like protein | |
| | 90,826,613 | IFIT1 | 10q23.3 | Interferon-induced protein with tetratricopeptide repeats 1 | |
| | 90,839,016 | IFIT5 | 10q23.3 | interferon-induced protein with tetratricopeptide repeats 5 | |
| | 90,854,633 | SLC16A12 | 10q23.3 | solute carrier family 16, member 12 | |
| | 91,007,326 | PANK1 | 10q23.3 | pantothenate kinase 1 | |
| | 91,125,951 | MPHOSPH1 | 10q23.3 | M-phase phosphoprotein 1 | |
| | 91,793,956 | HTR7 | 10q23.3 | 5-hydroxytryptamine (serotonin) receptor 7 | |
| | 92,295,852 | RPP30 | 10q23.3 | RNaseP protein p30 | |
| | 92,336,526 | ANKRD1 | 10q23.3 | ankyrin repeat domain 1 (cardiac muscle) | |
| RP11-67L13 | 92,644,946 | PCGF5 | 10q23.3 | polycomb group ring finger 5. Contains 1 RING-type zinc finger. | |
| | 92,834,678 | HECTD2 | 10q23.3 | HECT domain containing 2 | |
| | 93,052,778 | PPP1R3C | 10q23.3 | PP1 regulatory subunit 3C | |

TABLE 2

| | Anatomic Site | No. | Tumor Thickness [mm] (Range) | Gender M | Gender F | Median age Years, (Range) | No. of mutated BRAF (%)[1] | No. of mutated RAS (%)[1] | No. of wildtype BRAF & RAS (%)[1] | Common[2] Chromosomal Aberrations |
|---|---|---|---|---|---|---|---|---|---|---|
| non-CSD | Trunk | 20 | 3.6 (1.2-7.5) | 12 | 8 | 65 (28-82) | 14 (78) | 3 (17) | 1 (6) | enh (6p, 7, 8q, 17q, 20q) |
| | Lower Extremity | 12 | 2.8 (1.2-5.0) | 4 | 7 | 69 (21-84) | 4 (36) | 3 (27) | 4 (36) | dim (9p, 10, 21q) |
| | Upper Extremity | 6 | 4.0 (1.8-11.7) | 4 | 2 | 70 (11-85) | 2 (33) | 2 (33) | 2 (33) | |
| | Head | 1 | 2.7 (2.7-2.7) | 0 | 1 | 38 (38-38) | 1 (100) | 0 (0) | 0 (0) | |
| | NA | 1 | 3.7 (3.7-3.7) | 0 | 1 | 75 (75-75) | 1 (100) | 0 (0) | 0 (0) | |
| | Total | 40 | 3.1 (1.2-11.7) | 20 | 19 | 65 (11-85) | 22 (59) | 8 (22) | 7 (19) | |
| CSD | Head | 21 | 3.0 (1.0-7.5) | 9 | 10 | 76 (52-94) | 2 (10) | 4 (20) | 14 (70) | enh (6p, 11q13, 17q, 20q) |
| | Trunk | 3 | 1.7 (1.4-6.2) | 3 | 0 | 78 (76-84) | 0 (0) | 0 (0) | 1 (100) | dim (6q, 8p, 9p, 13, 21q) |
| | Upper Extremity | 3 | 3.8 (3.3-6.0) | 2 | 1 | 73 (67-83) | 0 (0) | 0 (0) | 3 (100) | |
| | NA | 3 | 3.0 (2.0-3.8) | 1 | 1 | 78 (73-82) | 1 (33) | 0 (0) | 2 (67) | |
| | Total | 30 | 3.0 (1.0-7.5) | 15 | 12 | 76 (52-94) | 3 (11) | 4 (15) | 20 (74) | |
| Mucosal | Total | 20 | 5.0 (3.8-45.0) | 7 | 13 | 68 (38-83) | 2 (11) | 1 (5) | 16 (84) | enh (1q, 6p, 7, 8q, 11q13, 17q, 20q) amp (1q31, 4q12 and 12q14) dim (3q, 4q, 6q, 8p, 9p, 10, 11p, 11q, 21q) |
| Acral | Sole | 27 | 2.9 (1.2-8.0) | 14 | 11 | 76 (34-90) | 3 (14) | 3 (14) | 16 (73) | enh (6p, 7, 8q, 17q, 20q) |
| | Subungual | 7 | 4.6 (2-10) | 5 | 2 | 66 (42-77) | 3 (43) | 0 (0) | 4 (57) | amp (5p15, 5p13, 11q13, 12q14) |
| | Palm | 1 | 1.0 (1.0-1.0) | 1 | 0 | 62 (62-62) | 1 (100) | 0 (0) | 0 (0) | dim (6q, 9p, 10, 11q, 21q) |
| | NA | 1 | 1.9 (1.9-1.9) | NA | NA | NA | NA (NA) | NA (NA) | NA (NA) | |
| | Total | 36 | 3.0 (1.0-10.0) | 20 | 13 | 73 (34-90) | 7 (23) | 3 (10) | 20 (67) | |

Abbreviations used:
enh: increased copy number;
dim: reduced copy number;
amp: amplification;
NA: not available;
CSD: chronic sun damage
[1]Percentages indicate proportion of samples which were sequenced successfully. Due to rounding some percentages do not add up to 100
[2]Aberrations that occur in at least 20% (dim, enh) or 10% (amp) of samples within individual groups.
Regions printed in bold occur at significantly different frequencies between groups (p < 0.05)

What is claimed is:

1. A method of detecting melanoma cells in a biological sample comprising melanocytes from a melanocytic lesion from a patient suspected of having melanoma, or having melanoma, the method comprising:
   contacting a nucleic acid sample from the biological sample from the patient with a probe that selectively hybridizes to a target nucleic acid sequence present on chromosomal region 6p24;
   and detecting the presence or absence of a gain in copy number of the target nucleic acid sequence on chromosomal region 6p24, thereby detecting melanoma cells if a gain of copy number is present.

2. The method of claim 1, wherein the biological sample is a skin sample.

3. The method of claim 1, wherein the biological sample is obtained from a patient that has melanoma and is from lymph node, lung, liver, adrenal gland, or bone.

4. The method of claim 1, wherein the contacting step comprises an amplification reaction.

5. The method of claim 1, wherein the contacting step comprises an in situ hybridization.

6. The method of claim 1, wherein the probe specifically hybridizes to a gene selected from the group consisting of PAK/1IP1; TFAP2A, GCNT2, or EDN1.

7. The method of claim 1, wherein the patient has melanoma.

8. The method of claim 1, wherein the biological sample is from lymph node.

* * * * *